United States Patent
Farascioni

(10) Patent No.: US 11,672,533 B2
(45) Date of Patent: Jun. 13, 2023

(54) LAPAROSCOPIC TRANSVERSE SURGICAL STAPLING SYSTEM

(71) Applicant: Covidien LP, Mansfield, MA (US)

(72) Inventor: David M. Farascioni, Bethel, CT (US)

(73) Assignee: COVIDIEN LP, Mansfield, MA (US)

( * ) Notice: Subject to any disclaimer, the term of this patent is extended or adjusted under 35 U.S.C. 154(b) by 346 days.

(21) Appl. No.: 17/014,421

(22) Filed: Sep. 8, 2020

(65) Prior Publication Data

US 2022/0071629 A1 Mar. 10, 2022

(51) Int. Cl.
*A61B 17/072* (2006.01)
*A61B 17/068* (2006.01)

(52) U.S. Cl.
CPC ........ *A61B 17/072* (2013.01); *A61B 17/0686* (2013.01); *A61B 2017/07257* (2013.01); *A61B 2017/07271* (2013.01)

(58) Field of Classification Search
CPC ........ A61B 17/072; A61B 2017/07271; A61B 2017/07257
USPC ...................................................... 227/175.2
See application file for complete search history.

(56) References Cited

U.S. PATENT DOCUMENTS

| | | | | |
|---|---|---|---|---|
| 4,354,628 A * | 10/1982 | Green | .................. | A61B 17/072 227/19 |
| 4,665,916 A * | 5/1987 | Green | .................. | A61B 17/072 227/19 |
| 5,588,579 A * | 12/1996 | Schnut | ................. | A61B 17/115 227/19 |
| 8,286,847 B2 * | 10/2012 | Taylor | .............. | A61B 17/07207 227/176.1 |
| 9,675,356 B2 * | 6/2017 | Racenet | ............... | A61B 17/105 |
| 10,004,504 B2 * | 6/2018 | Bryant | ................. | A61B 17/072 |
| 10,575,849 B2 * | 3/2020 | Heinrich | .......... | A61B 17/07207 |
| 2001/0030219 A1 * | 10/2001 | Green | ............. | A61B 17/07207 227/175.1 |
| 2005/0203548 A1 * | 9/2005 | Weller | ............ | A61B 17/07207 606/139 |

(Continued)

FOREIGN PATENT DOCUMENTS

| | | |
|---|---|---|
| EP | 1722691 A1 | 11/2006 |
| EP | 2574285 A1 | 4/2013 |

(Continued)

OTHER PUBLICATIONS

Transverse vs. perpendicular—Wikipedia. URL https://en.wikipedia.org/wiki/Geometric_terms_of_location#:~:text=Perpendicular%20%E2%80%93%20at%20right%20angles%20to,any%20angle%2C%20i.e.%20not%20parallel. (Year: 2022).*

(Continued)

*Primary Examiner* — Valentin Neacsu
(74) *Attorney, Agent, or Firm* — Carter, DeLuca & Farrell LLP

(57) ABSTRACT

A transverse surgical stapling system includes an elongated shaft assembly, a distal tube, an anvil assembly, and a cartridge assembly. The distal tube has a proximal end portion and a distal end portion. The proximal end portion of the distal tube supports the elongated shaft assembly. The anvil assembly is supported on the distal end portion of the distal tube. The cartridge assembly is supported on the distal tube in movable relation to the anvil assembly. The anvil and cartridge assemblies are movable between retracted and extended positions relative to the distal tube.

18 Claims, 17 Drawing Sheets

(56) References Cited

U.S. PATENT DOCUMENTS

| | | | | |
|---|---|---|---|---|
| 2007/0084899 A1* | 4/2007 | Taylor | ............... | A61B 17/07207 227/176.1 |
| 2008/0054045 A1* | 3/2008 | Milliman | ............. | A61B 17/115 227/175.1 |
| 2008/0294179 A1* | 11/2008 | Balbierz | ................ | A61B 17/10 606/151 |
| 2009/0082785 A1* | 3/2009 | Milliman | ........... | A61B 17/1155 606/139 |
| 2011/0295269 A1* | 12/2011 | Swensgard | ............ | A61B 34/76 606/130 |
| 2012/0116416 A1* | 5/2012 | Neff | ....................... | A61B 34/35 606/130 |
| 2012/0234890 A1* | 9/2012 | Aronhalt | .......... | A61B 17/00234 227/175.1 |
| 2014/0144969 A1* | 5/2014 | Scheib | ............... | A61B 17/1155 227/175.1 |
| 2015/0238193 A1* | 8/2015 | Balbierz | ............. | A61B 17/1114 227/176.1 |
| 2017/0189015 A1* | 7/2017 | Adams | ................. | A61B 17/072 |
| 2018/0168574 A1* | 6/2018 | Robinson | ......... | A61B 17/07207 |
| 2018/0235635 A1* | 8/2018 | Rekstad | ............... | A61B 17/072 |
| 2018/0325508 A1* | 11/2018 | Aronhalt | .......... | A61B 17/07207 |
| 2022/0071629 A1* | 3/2022 | Farascioni | ........... | A61B 17/072 |

FOREIGN PATENT DOCUMENTS

| | | |
|---|---|---|
| EP | 3478189 A2 | 5/2019 |
| WO | 2008141288 A1 | 11/2008 |
| WO | 2012125615 A2 | 9/2012 |
| WO | 2016025132 A1 | 2/2016 |

OTHER PUBLICATIONS

Torsion Springs, URL https://www.overheaddoorpdx.com/the-spring-torsion-vs-extension/ (Year: 2016).*

Extended European Search Report for Application No. 21195367.4 dated Feb. 4, 2022.

* cited by examiner

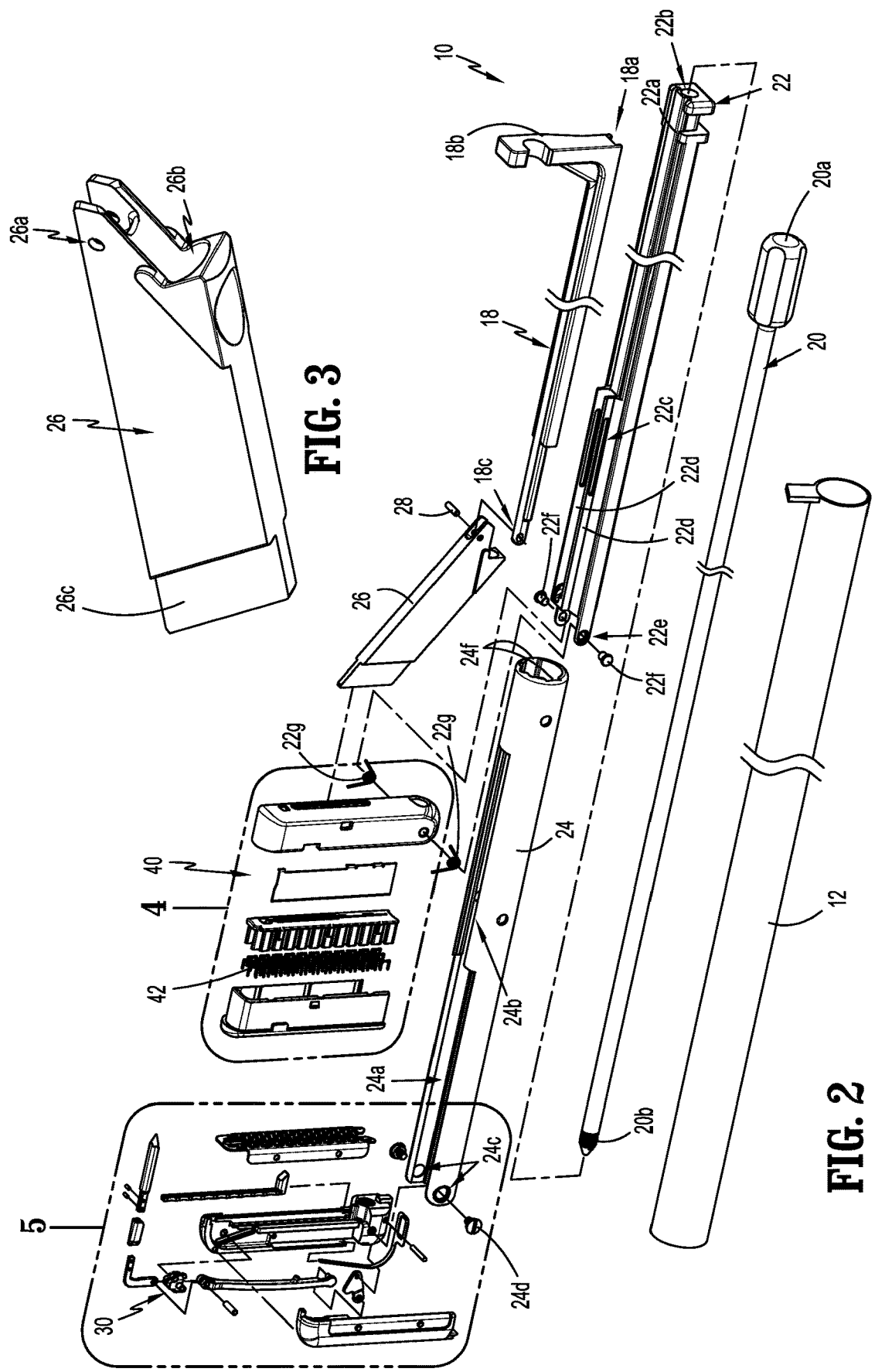

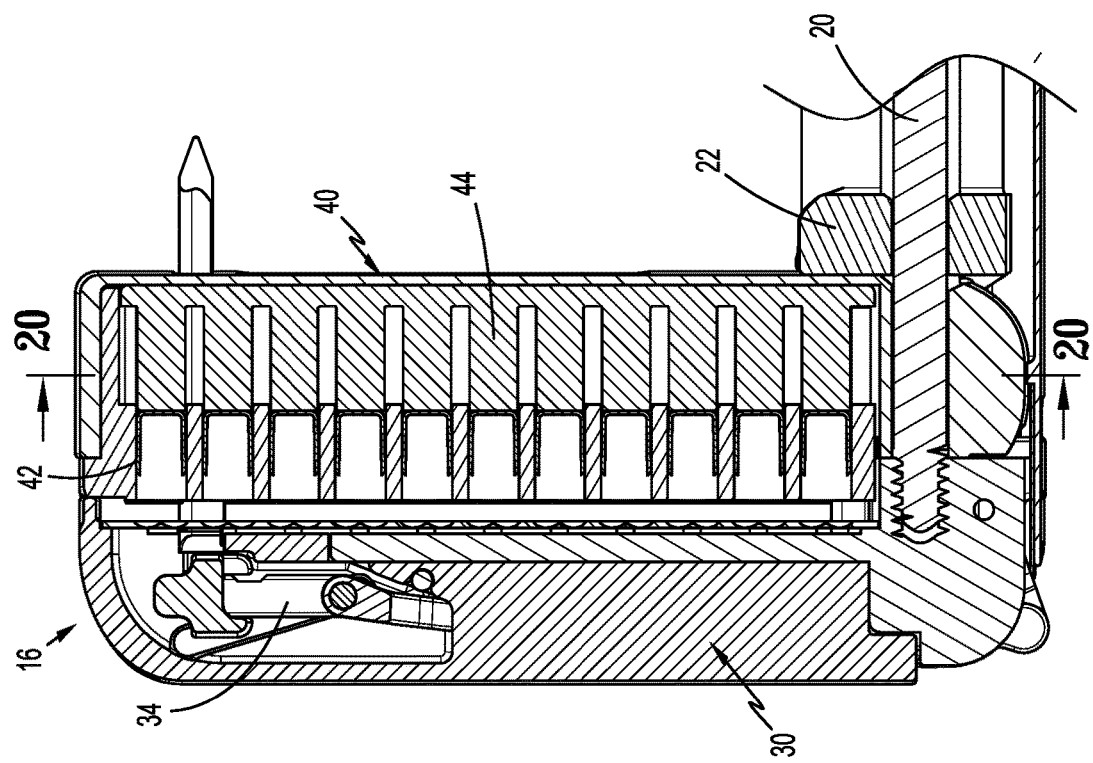
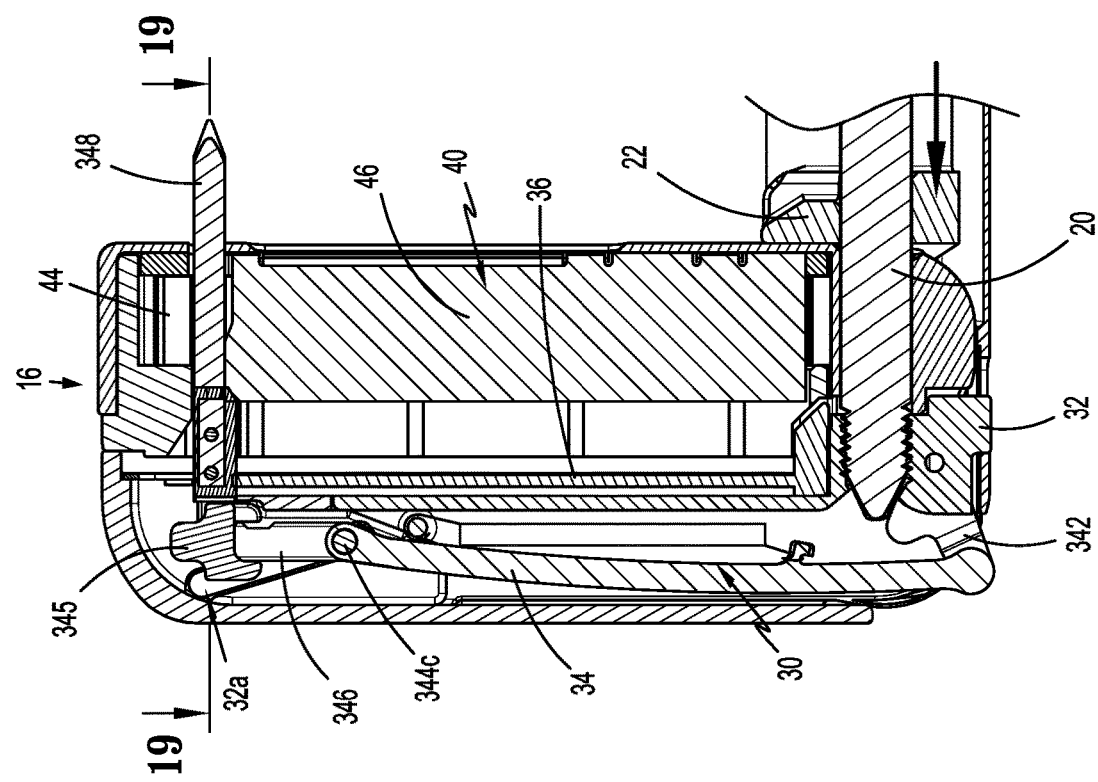

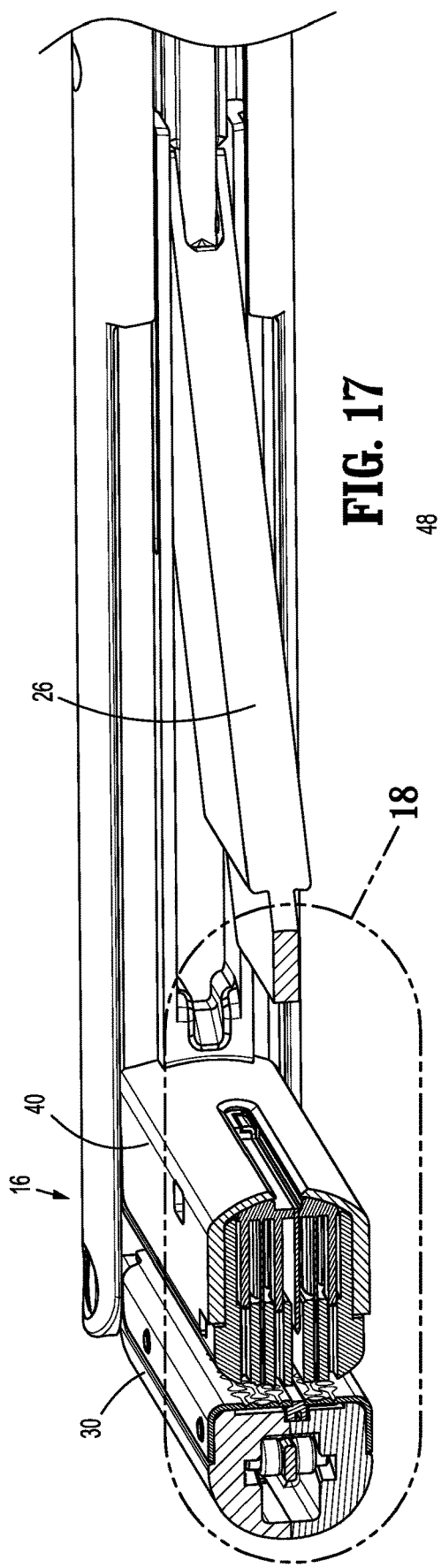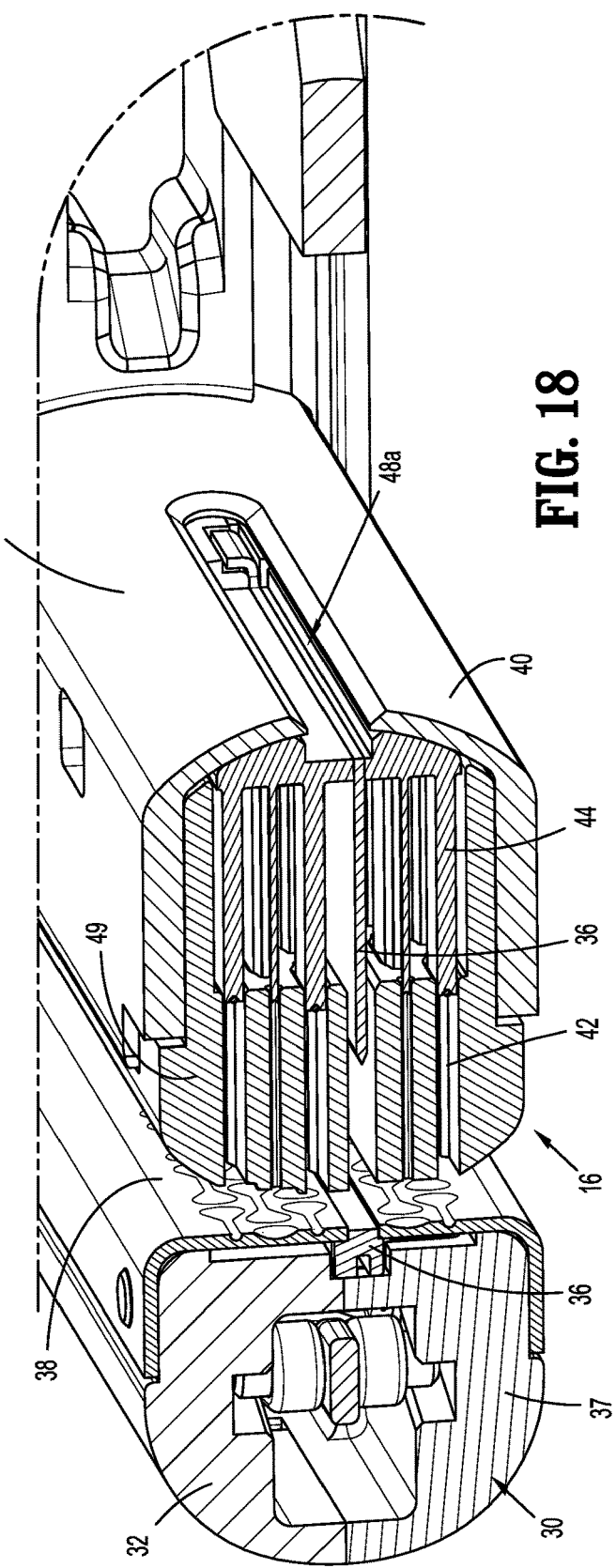

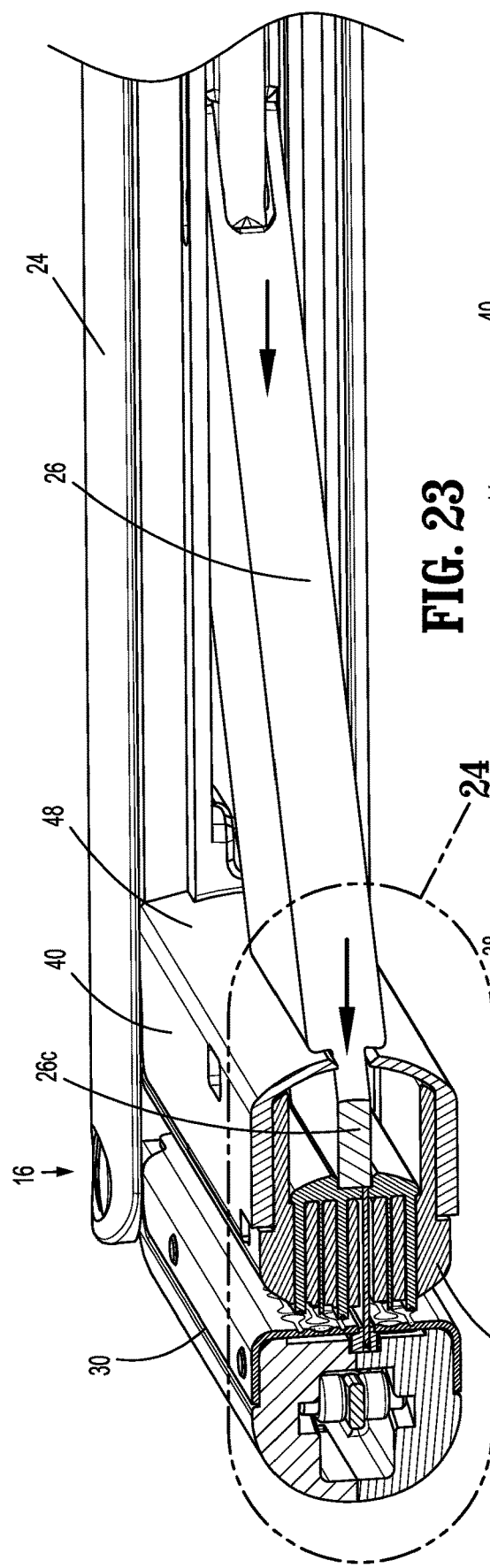
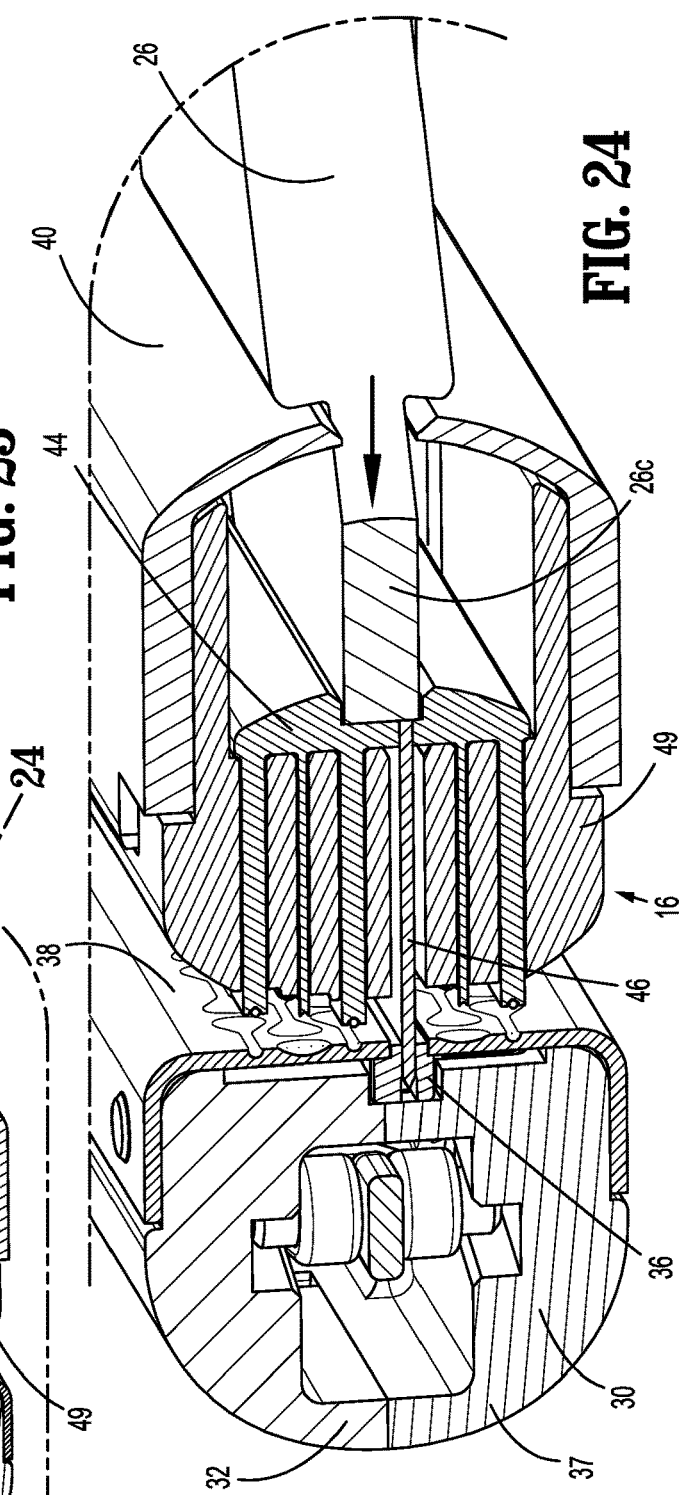

LAPAROSCOPIC TRANSVERSE SURGICAL STAPLING SYSTEM

TECHNICAL FIELD

This disclosure relates to surgical stapling systems and, more particularly, to transverse surgical stapling systems for clamping, severing, and joining tissue.

BACKGROUND

Fasteners have traditionally been used to replace suturing when joining various body structures. Surgical stapling systems employed to apply these fasteners are generally designed to simultaneously cut and seal tissue to reduce the time and risks involved with surgical procedures. Surgical stapling systems that clamp, cut and/or staple tissue are well known in the art. These surgical stapling instruments are employed, for example, for fastening tissue or organs prior to transection or resection or during anastomoses. In some cases, these surgical stapling instruments are utilized for occluding organs in thoracic and abdominal procedures.

Such surgical stapling instruments can include an anvil assembly, a cartridge assembly for supporting an array of surgical staples, an approximation mechanism for approximating the cartridge and anvil assemblies, an alignment or guide pin assembly for capturing tissue between the cartridge and anvil assemblies and for maintaining alignment between the cartridge and anvil assemblies during approximation and firing, and a firing mechanism for ejecting the surgical staples from the cartridge assembly.

SUMMARY

According to one aspect of this disclosure, a transverse surgical stapling system includes an elongated shaft assembly, a distal tube, an anvil assembly, and a cartridge assembly. The distal tube has a proximal end portion and a distal end portion. The proximal end portion of the distal tube supports the elongated shaft assembly. The anvil assembly is supported on the distal end portion of the distal tube. The cartridge assembly is supported on the distal tube in movable relation to the anvil assembly. The anvil and cartridge assemblies are movable between retracted and extended positions relative to the distal tube.

In aspects of this disclosure, the cartridge assembly may be spring biased toward the extended position thereof by a torsion spring. The anvil assembly may be spring biased toward the extended position thereof by a leaf spring.

In aspects of this disclosure, the elongated shaft assembly may include a locking rod that is receivable by the anvil and cartridge assemblies to lock the anvil and cartridge assemblies in the extended positions thereof.

In aspects of this disclosure, the elongated shaft assembly may include a clamping rod that may be pivotally coupled to the cartridge assembly. The clamping rod may be positioned to translate the cartridge assembly relative to the anvil assembly.

In aspects of this disclosure, the elongated shaft assembly may include a firing rod that translates through the distal tube to fire the staples from the cartridge assembly. The firing rod may include a firing wedge pivotally coupled to a distal end portion of the firing rod. The firing wedge may be positioned to engage the cartridge assembly. The firing wedge may be positioned to pivot between a retracted position within the distal tube and an extended position in which a distal end of the firing wedge extends from the distal tube at an acute angle relative to the distal tube.

In aspects of this disclosure, the anvil assembly may include an alignment pin assembly that is positioned to engage the cartridge assembly. The alignment pin assembly may include an alignment pin that is pivotally coupled to the anvil assembly and positioned to move between a retracted position within the anvil assembly and an extended position in which the alignment pin extends from the anvil assembly transverse to an anvil of the anvil assembly.

According to another aspect of this disclosure, a surgical stapling system includes a distal tube defining a longitudinal axis, an outer tube slidably supported on the distal tube, an elongated shaft assembly, an anvil assembly, and a cartridge assembly supported on the distal tube and movable relative to the anvil assembly. The cartridge assembly is movable between a first position aligned with longitudinal axis and a second position transverse to the longitudinal axis.

In aspects of this disclosure, the cartridge assembly may be spring biased toward the second position thereof.

In aspects of this disclosure, the outer tube may be movable in a proximal direction to enable the cartridge assembly to move from the first position to the second position.

In aspects of this disclosure, the elongated shaft assembly may include a locking rod that is receivable by the cartridge assembly to prevent the cartridge assembly from pivoting relative to the longitudinal axis.

In aspects of this disclosure, the elongated shaft assembly may include a clamping rod that is pivotally coupled to the cartridge assembly. The clamping rod may be positioned to translate the cartridge assembly relative to the anvil assembly.

According to still another aspect of this disclosure, a transverse surgical stapling system includes a distal tube defining a longitudinal axis, an outer tube slidably supported on the distal tube, an elongated shaft assembly, a cartridge assembly supporting a plurality of staples, and an anvil assembly supported on the distal tube. The anvil assembly is pivotable between a retracted position aligned with the distal tube and an extended position in which the anvil assembly extends transverse to the distal tube. In the extended position, the anvil assembly is positioned to form the staples supported in the cartridge assembly.

In aspects of this disclosure, the elongated shaft assembly may include a firing rod that translates through the distal tube to fire the staples from the cartridge assembly. The firing rod may include a firing wedge pivotally coupled to a distal end portion of the firing rod. The firing wedge may be positioned to engage the cartridge assembly. The firing wedge may be positioned to pivot between a retracted position within the distal tube and an extended position in which a distal end of the firing wedge extends from the distal tube at an acute angle relative to the distal tube.

In aspects of this disclosure, the anvil assembly may include an alignment pin that is pivotally coupled to the anvil assembly and positioned to move between a retracted position and an extended position for selectively engaging the cartridge assembly.

Other aspects, features, and advantages will be apparent from the description, the drawings, and the claims that follow.

BRIEF DESCRIPTION OF DRAWINGS

The accompanying drawings, which are incorporated in and constitute a part of this specification, illustrate aspects of the disclosure and, together with a general description of the disclosure given above and the detailed description given below, serve to explain the principles of this disclosure, wherein:

FIG. 2 is a perspective view, with parts separated, of the surgical stapling system of FIG. 1;

FIG. 3 is an enlarged, perspective view of a firing wedge of the surgical stapling system of FIG. 1;

FIGS. 11-24 are progressive views illustrating a firing of the surgical stapling system of FIG. 1.

DETAILED DESCRIPTION

Figure 1:
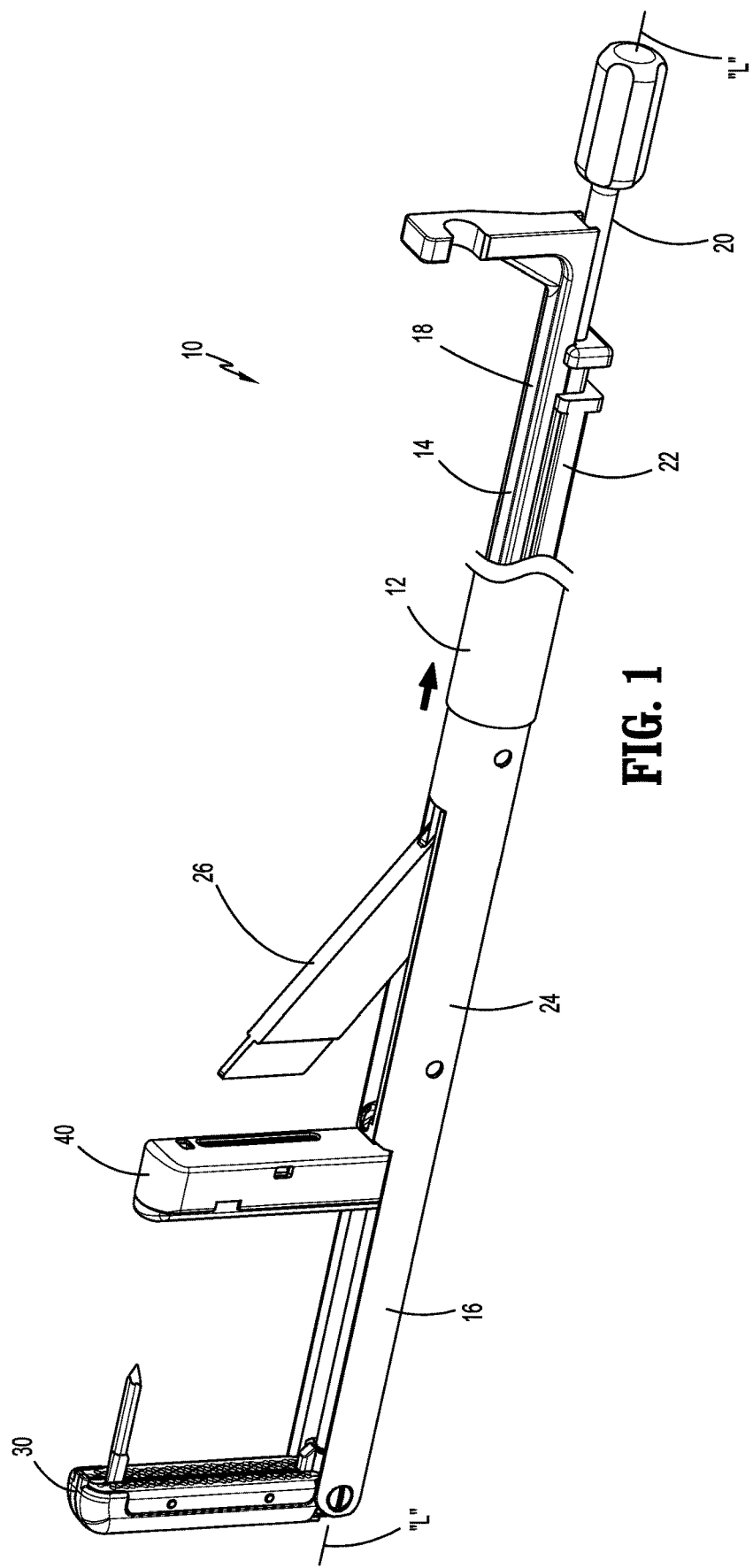
FIG. 1 is a perspective view of an illustrative surgical stapling system in accordance with the principles of this disclosure.

Aspects of the disclosed surgical stapling systems are described in detail with reference to the drawings, in which like reference numerals designate identical or corresponding elements in each of the several views. As commonly known, the term "clinician" refers to a doctor, a nurse, or any other care provider and may include support personnel. Additionally, the term "proximal" refers to the portion of structure that is closer to the clinician and the term "distal" refers to the portion of structure that is farther from the clinician. In addition, directional terms such as front, rear, upper, lower, top, bottom, and the like are used simply for convenience of description and are not intended to limit the disclosure attached hereto.

In the following description, well-known functions or constructions are not described in detail to avoid obscuring the present disclosure in unnecessary detail.

Further, although the surgical instrumentation described herein is provided in connection with a manual surgical stapling system for brevity, the disclosed surgical stapling system may be powered and/or or robotically-controlled. For a detailed description of the structure and function of exemplary surgical stapling systems, one or more components of which may be included, or modified for use with the disclosed aspects, reference may be made to U.S. Pat. No. 10,575,849, 10,004,504, or U.S. Pat. No. 9,675,356, the entire contents of each of which are incorporated herein by reference.

Briefly, this disclosure details structure and methods for effectuating open and laparoscopic surgical stapling procedures such as a low anterior resection ("LAR"). LAR is a surgery often performed to treat cancer of the rectum where the cancerous portion of the rectum is removed so that the remaining healthy portions of the rectum can be reconnected to the colon with a surgical stapling apparatus. Typically, this procedure is performed as an open procedure. Advantageously, the disclosed surgical stapling system enables a clinician to perform such procedure either openly or laparoscopically. In particular, the disclosed surgical stapling system includes anvil and cartridge assemblies that are movable between a retracted position for insertion through a surgical cannula assembly or trocar, and an extended position in which the anvil and cartridge assemblies extend laterally from the surgical stapling system (e.g., in a guillotine-type stapler arrangement) for clamping, cutting, and stapling tissue therebetween when fired.

Figure 6:
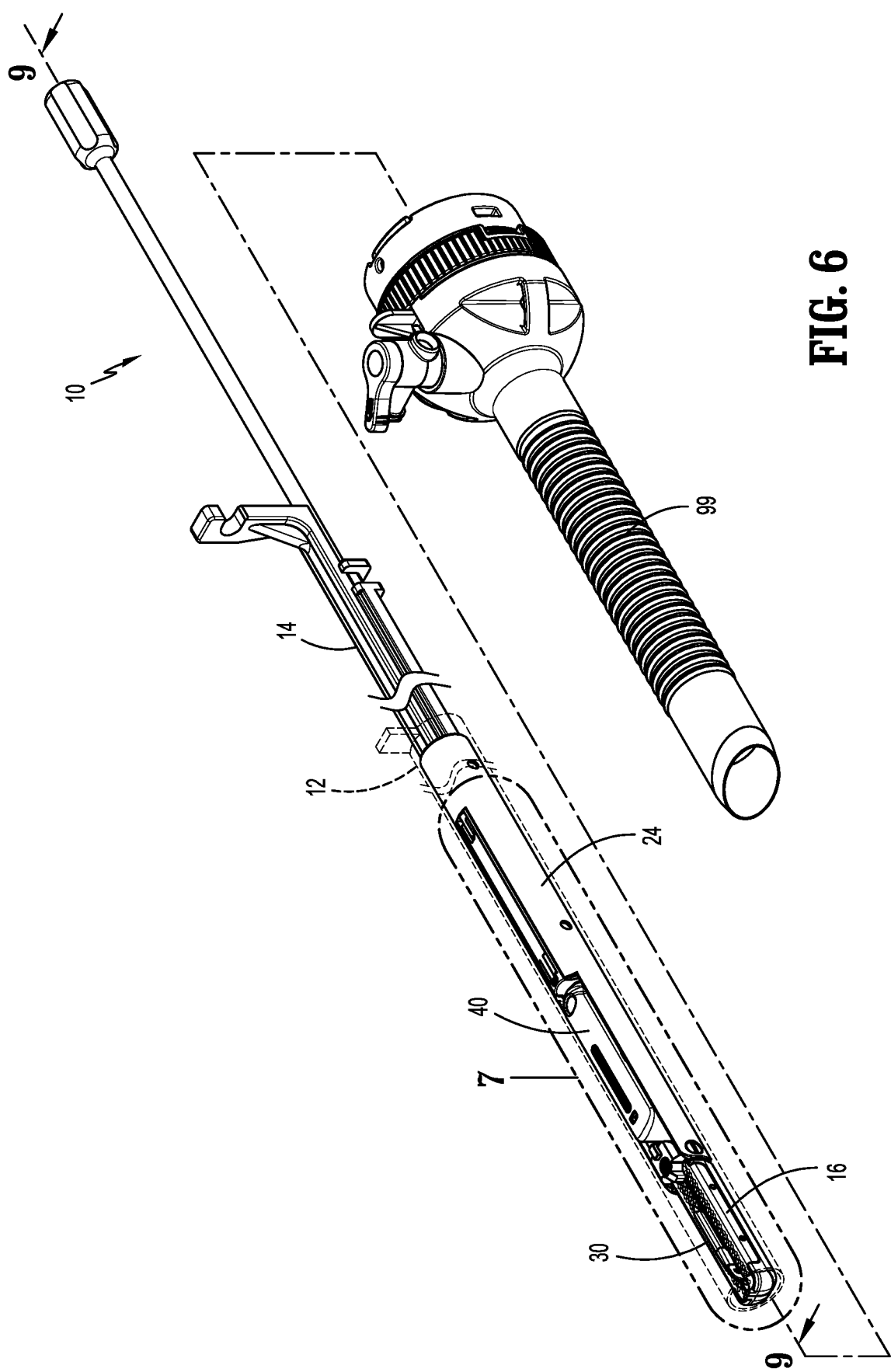
FIG. 6 is perspective view of the surgical stapling system of FIG. 1 in relation to a surgical cannula assembly, the surgical stapling system illustrated in a first position with an outer tube of the surgical stapling system shown in phantom for clarity.
Figure 7:
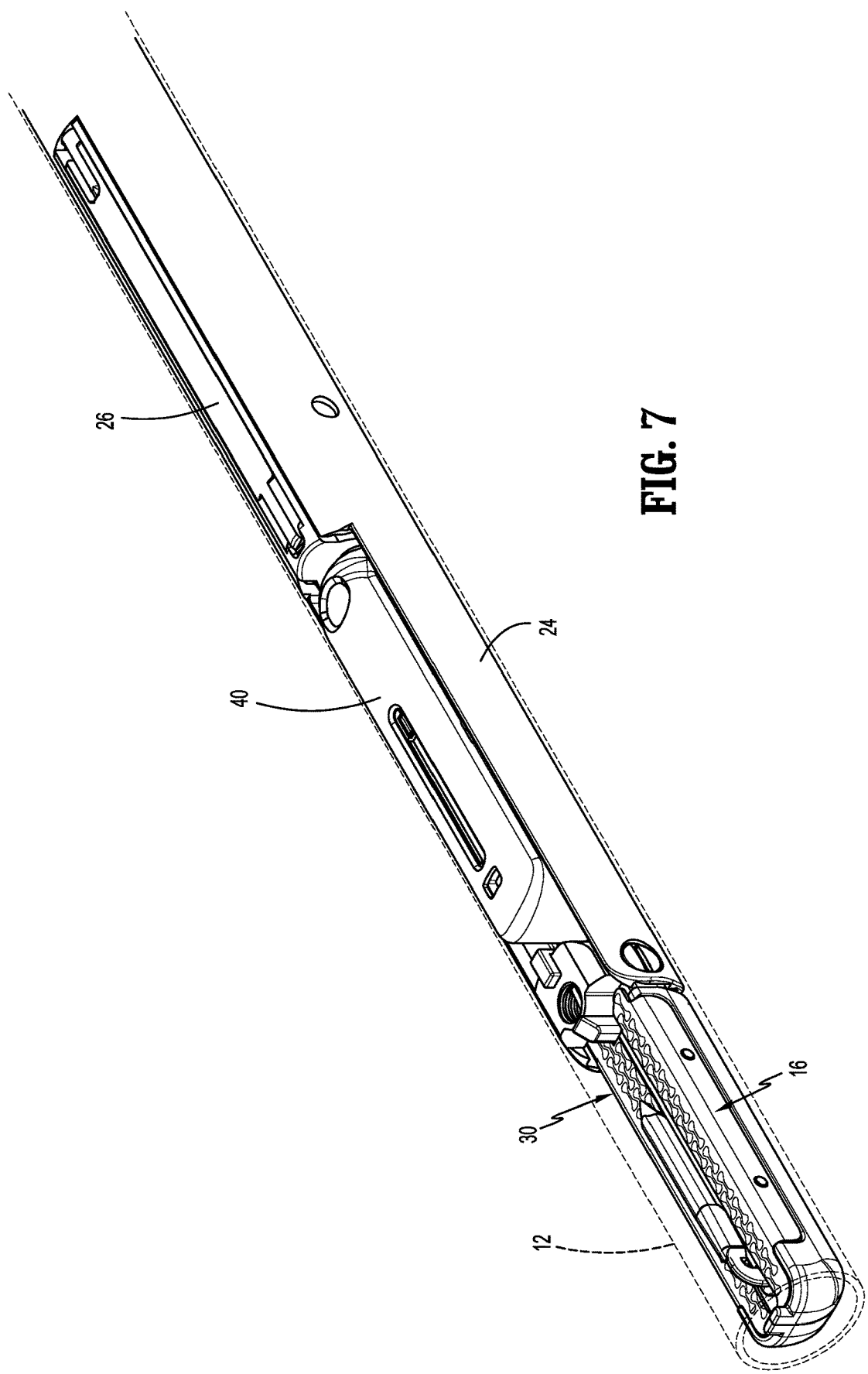
FIG. 7 is an enlarged, perspective view of the indicated area of detail shown in FIG. 6.

With reference to FIGS. 1-3, a surgical stapling system 10 of this disclosure includes a housing tube 12 supported on an elongated shaft assembly 14 and positioned for relative axial movement between one another. Elongated shaft assembly 14 extends distally to an end effector 16 and defines a longitudinal axis "L" therealong. End effector 16 includes an anvil assembly 30 and a cartridge assembly 40 that are moveable between retracted and extended positions for selective advancement thorough, for example, a surgical cannula assembly or trocar 99 to access a surgical site within tissue "T" (see FIGS. 6 and 8). Cartridge assembly 40 houses a plurality of staples 42 for forming against anvil assembly 30 upon a firing of surgical stapling system 10. Elongated shaft assembly 14 includes a firing rod 18 for firing staples 42, a locking rod 20 for maintaining anvil and cartridge assemblies 30, 40 in an extended position, and clamping rod 22 for moving cartridge assembly 40 relative to anvil assembly 30 to clamp tissue therebetween.

Firing rod 18, locking rod 20, and clamping rod 22 of elongated shaft assembly 14 are movably supported within a distal tube 24 on a proximal end portion of distal tube 24. Firing rod 18 defines a guide channel 18a on a bottom surface thereof that slidably supports firing rod 18 on a support rib 22a extending axially along clamping rod 22. Firing rod 18 further includes a drive handle 18b on a proximal end portion thereof and a pin hole 18c on a distal end portion thereof.

Locking rod 20 is slidably and rotatably disposed within a lumen 22b defined through clamping rod 22. Locking rod 20 includes a gripping handle 20a on a proximal end portion thereof and a threaded tip 20b on a distal end portion thereof.

Pin hole 18c on the distal end portion of firing rod 18 and pin holes 26a of a firing wedge 26 receive a pivot pin 28 therethrough to pivotally couple firing rod 18 and firing wedge 26 together to enable firing wedge 26 to pivot between retracted and extended positions. Firing wedge 26 further defines an angled rod channel 26b through a proximal end portion thereof that receives locking rod 20 therethrough to lock firing wedge 26 in the extended position thereof. Firing wedge 26 extends distally to a firing tooth 26c.

Clamping rod 22 defines pin channels 22c through raised tracks 22d of clamping rod 22 that laterally support firing wedge 26 therebetween. Pin channels 22c slidably support pivot pin 28 therein to facilitate axial movement of firing rod 18 and firing wedge 26 relative to clamping rod 22. A distal end portion of clamping rod 22 further includes pin holes 22e defined therein that accommodate pivot pins 22f for securing the distal end portion of clamping rod 22 to cartridge assembly 40. Pivot pins 22f are coupled to torsion springs 22g that spring bias or urge cartridge assembly 40 in the extended position thereof.

Distal tube 24 defines an open distal channel 24a and an open proximal channel 24b therealong. Open proximal channel 24b is raised above open distal channel 24a and is positioned to enable firing wedge 26 to move between extended and retracted positions relative to distal tube 24. Distal channel 24a is positioned to enable anvil and cartridge assemblies 30, 40 to move between their respective extended and retracted positions relative to distal tube 24. Distal tube 24 further defines pin openings 24c therethrough that receive threaded pivot pins 24d for enabling anvil assembly 30 to pivot relative to a distal end of distal tube 24 between the extended and retracted positions thereof. Distal tube 24 further defines inner side channels 24f along an inner surface thereof for slidably receiving clamping rod 22.

Figure 4:
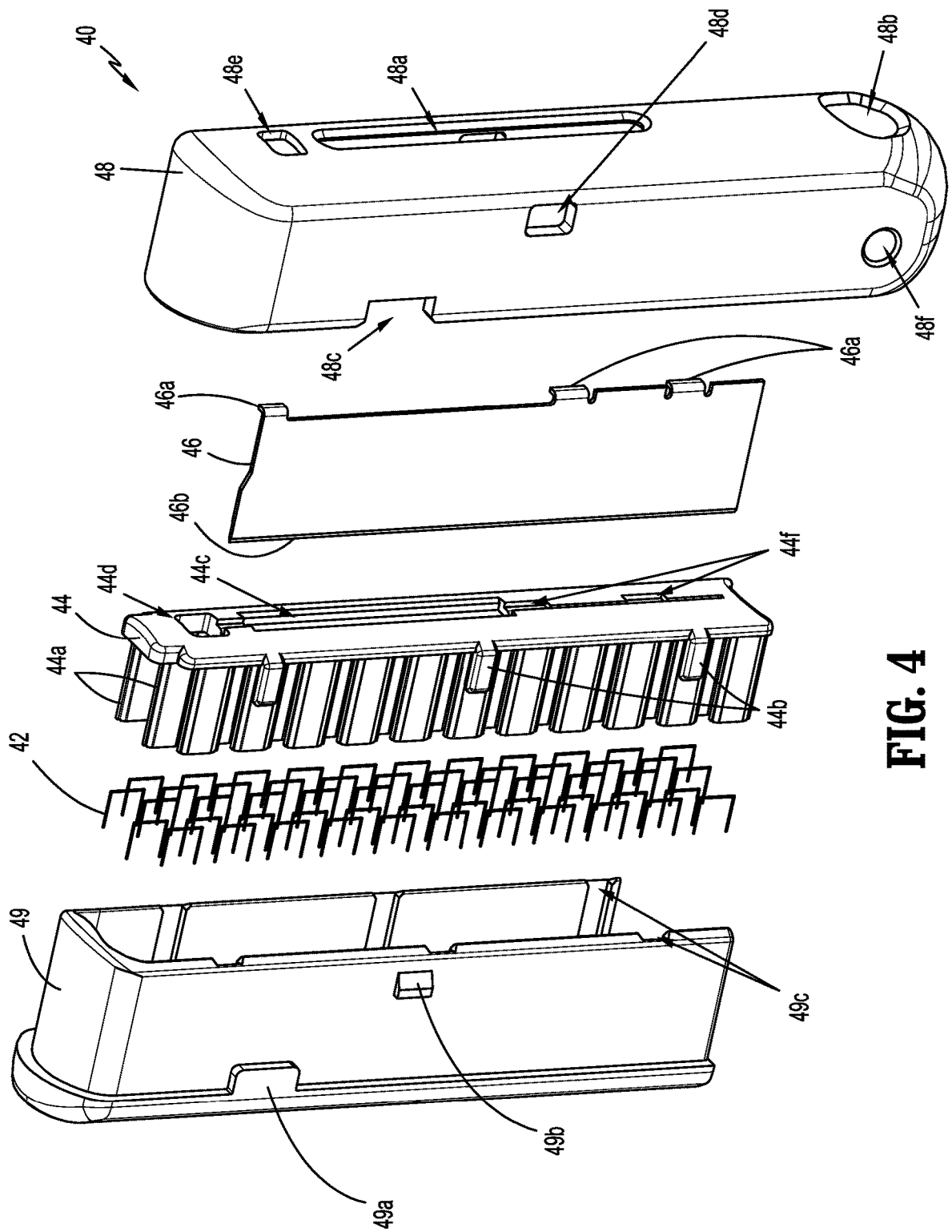
FIGS. 4 and 5 are enlarged, perspective views, with parts separated, of the indicated areas of detail shown in FIG. 2.

Turning now to FIG. 4, cartridge assembly 40 of end effector 16 supports staples 42, a pusher 44, and a knife 46. Cartridge assembly 40 includes a proximal housing 48 and a distal housing 49. Staples 42 are disposed in a plurality of rows. Pusher 44 includes a plurality of pusher bars 44a that align with the plurality of rows of staples 42. Pusher 44 includes guide tabs 44b that facilitate alignment with distal housing 49 and defines a knife slot 44c along a spine thereof for receiving knife 46 therethrough. Pusher 44 also defines an alignment pin hole 44d therethrough and knife tab recesses 44f at spaced apart locations along knife slot 44c. Knife 42 includes proximal tabs 46a that seat in the knife tab recesses 44f of pusher 44 and a distal cutting edge 46b. Proximal housing 48 defines an elongate wedge channel 48a along a spine thereof for receiving firing wedge 26 therein and a threaded rod passage 48b for receiving locking rod 20 therethrough to lock cartridge assembly 40 in the extended position thereof. Proximal housing 48 further includes alignment recesses 48c and mounting apertures 48d that enable alignment and securement of proximal housing 48 to distal housing 49. Proximal housing 48 also includes an alignment pin hole 48e disposed in registration with alignment pin hole 44d of pusher 44. In addition, proximal housing 48 defines pivot pin holes 48f that receive pivot pins 22f therein to enable cartridge assembly 40 to rotate between the retracted and extended positions thereof. Distal housing 49 includes alignment tabs 49a that are received in alignment recess 48c of proximal housing 48 to align proximal and distal housings 48, 49 together. Mounting tabs 49b extend from sidewalls of distal housing 49 and are receivable within mounting apertures 48d of proximal housing 48 to secure proximal and distal housings 48, 49 together. A plurality of guide channels 49c are defined along an inner surface of distal housing 49 for receiving guide tabs 44b of pusher 44 therein.

Figure 11:
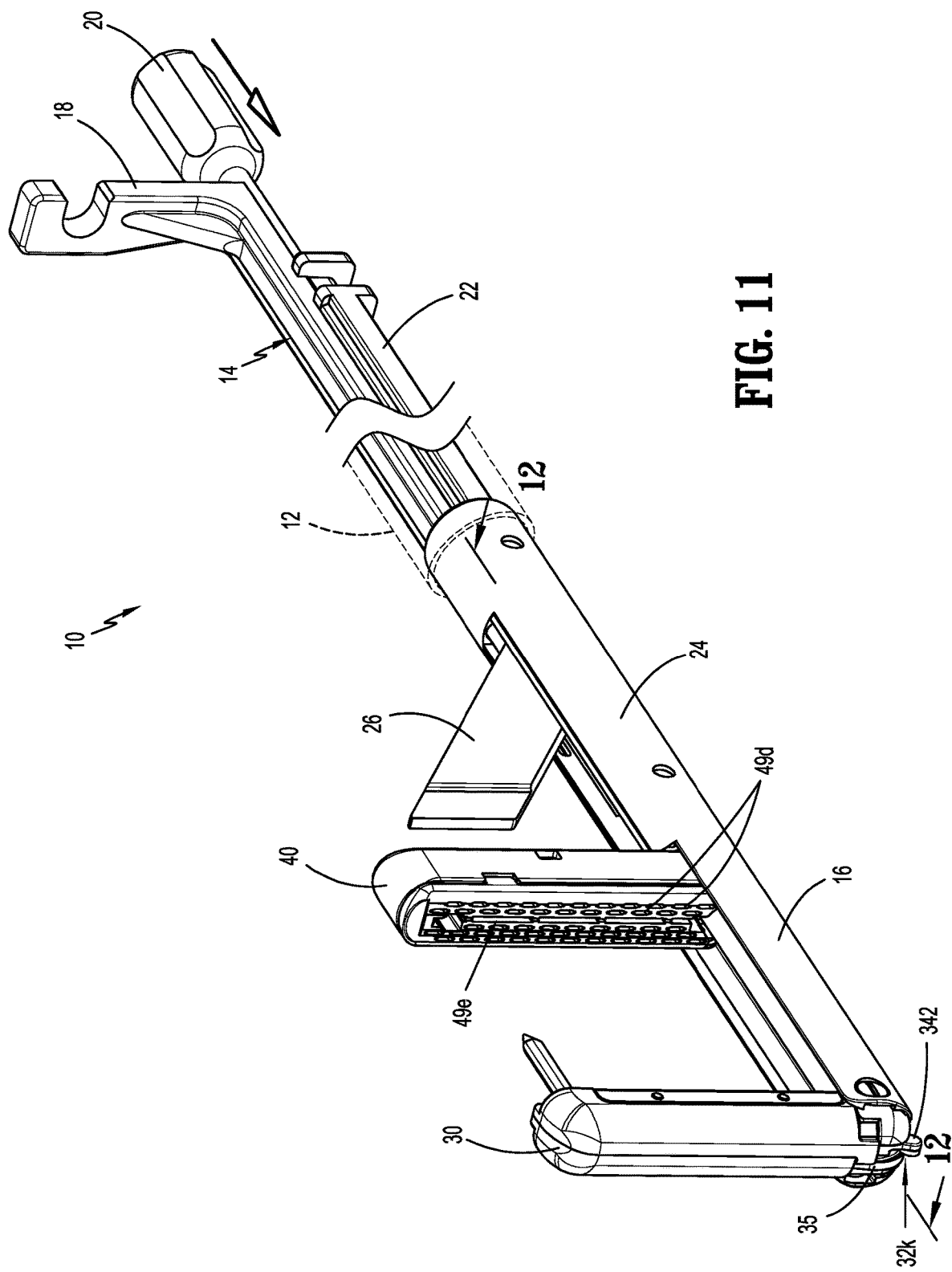

With brief reference to FIG. 11, distal housing 49 also defines a plurality of rows of staple retention slots 49d and a knife slot 49e in a distal face or tissue contacting surface thereof. The plurality of rows of staple retention slots 49d are disposed in registration with the plurality of staples 42 for enabling staples 42 to be fired therethrough.

Figure 5:
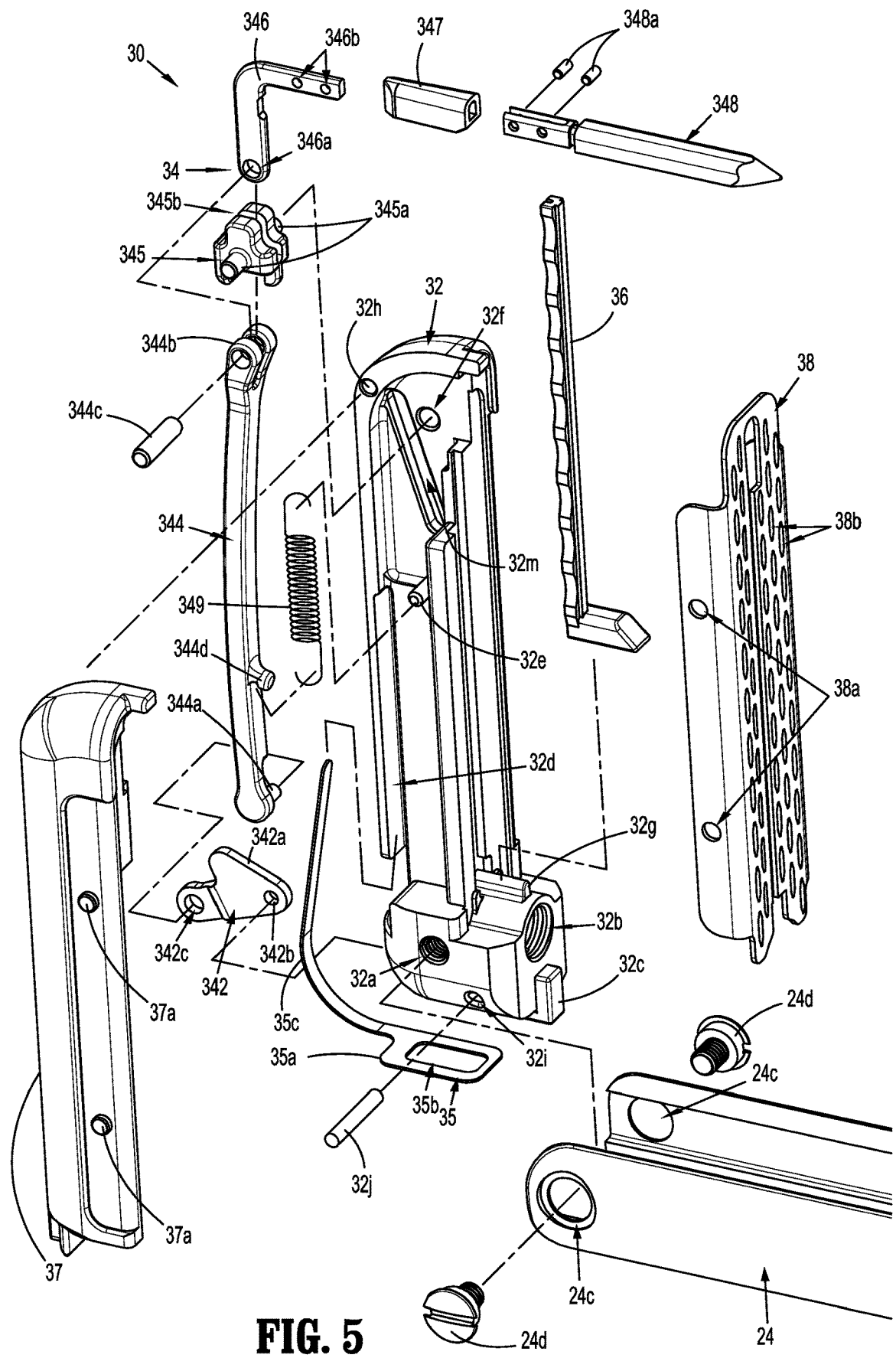

Referring now to FIG. 5, anvil assembly 30 of end effector 16 includes a first housing 32, an alignment pin assembly 34, a leaf spring 35, a knife stop 36, a second housing 37, and an anvil 38. First housing 32 of anvil assembly 30 defines threaded pivot pin holes 32a that receive pivot pins 24d and threaded pivot pins 24d and a threaded rod aperture 32b positioned to receive threaded tip 20b of locking rod 20. First housing 32 further includes a leaf spring mount 32c and defines a leaf spring channel 32d that facilitate securement of leaf spring 35 to first housing 32. First housing 32 also includes a spring post 32e and defines a coupler pin aperture 32f for supporting alignment pin assembly 34. First housing 32 further includes a knife stop ledge 33g that supports knife stop 36 on first housing 32 and defines attachment apertures 32h that facilitate securement of first and second housings 32, 37 together (e.g., via various pins and/or posts extending between first and second housings 32, 37 that are receivable within attachment apertures 32h). First housing 32 also includes a pivot pin opening 32i and a pivot plate slot 32k (see FIG. 11) that receives a pivot pin 32j to couple alignment pin assembly 34 in first housing 32 and to facilitate pivoting movement of alignment pin assembly 34 relative to first housing 32. First housing 32 further includes an angled slide channel 32m defined therethrough. Second housing 37 includes an angled slide channel 32m in mirrored relation to angled slide channel 32m of first housing 32.

Leaf spring 35 includes a snare portion 35a with a snare opening 35b defined therethrough to enable snare portion 35a to secure to leaf spring mount 32c of first housing 32. Leaf spring 35 also includes a spring finger 35c that extends from snare portion 35a and is received in leaf spring channel 32d of first housing 32. Spring finger 35c is movable between a flexed position in which a distal end of spring finger 35c is aligned with snare portion 35a and parallel to longitudinal axis "L" of surgical stapling apparatus 10, and an unflexed position (see FIG. 5) in which the distal end of spring finger 35 is transverse to snare portion 35a and to longitudinal axis "L" of surgical stapling apparatus 10. Leaf spring 35 is positioned to bias or urge anvil assembly 30 in the extended position thereof where anvil assembly 30 is transverse to longitudinal axis "L" of surgical stapling apparatus 10.

Alignment pin assembly 34 of anvil assembly 30 includes a pivot plate 342, a drive arm 344, a coupler 345, an elbow 346, a collar 347, an alignment pin 348, and a compression spring 349. Pivot plate 342 includes a drive ramp 342a and first pin openings 342b that couples to pivot pin 32j and a second pin opening 342c that couples to drive arm 344. Drive arm 344 includes pivot plate post 344a on a first end thereof that couples to second pin opening 342c of pivot plate 342 and a clevis 344b on a second end thereof that receives pivot pin 344c therethrough. Driver arm 344 also includes spring nub 344d to which a first end of spring 349 couples. A second end of spring 349 couples to spring post 32e of first housing 32. Coupler 345 mounts to clevis 344b of driver arm 344 and includes side pins 345a that extend therefrom for securing to coupler pin aperture 32f of first housing 32 and a corresponding aperture (not shown) defined in second housing 37. Coupler 345 further defines an elbow slot 345b therebetween that receives elbow 346 therein for coupling elbow 346 to clevis 344b of driver arm 344 by pin 344c. Elbow 346 defines a pin hole 346a on a first end thereof that receives pin 344c therein. Elbow 346 also defines pin holes 346b on a second end thereof for receiving pins 348a therein. Collar 347 couples to elbow 346 and alignment pin 348 to maintain pins 348a in position and secure alignment pin 348 to elbow 346. First and second housings 32, 37 include mounting nubs 37a that retain anvil 38 to first and second housings 32, 37 via nub openings 38a defined through anvil 38. Anvil 38 further defines a plurality of rows of staple forming pockets 38b in a tissue contacting surface thereof.

Figure 8:
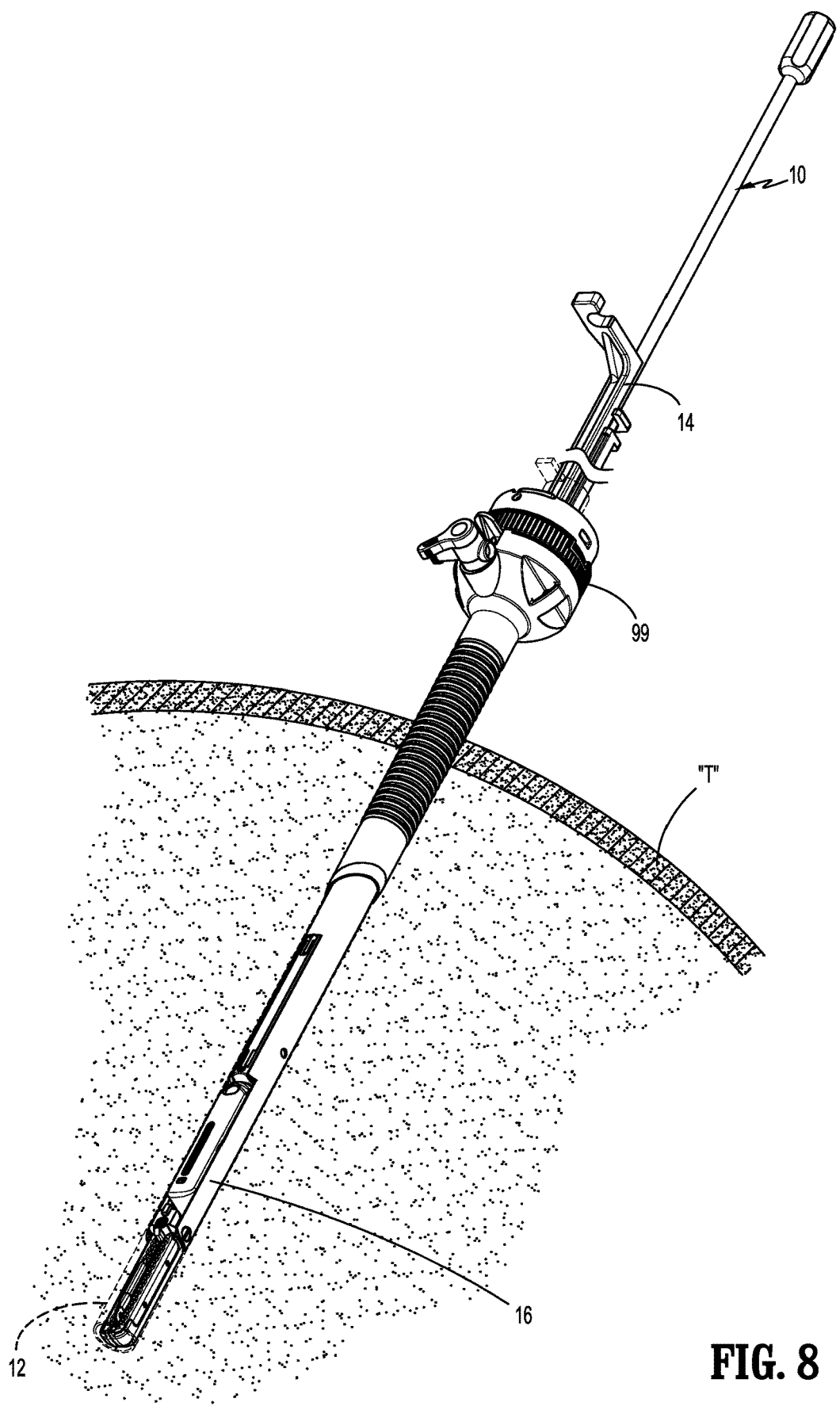
FIG. 8 is a perspective view illustrating the surgical stapling system inserted through the surgical cannula assembly of FIG. 6 and into tissue.
Figure 9:
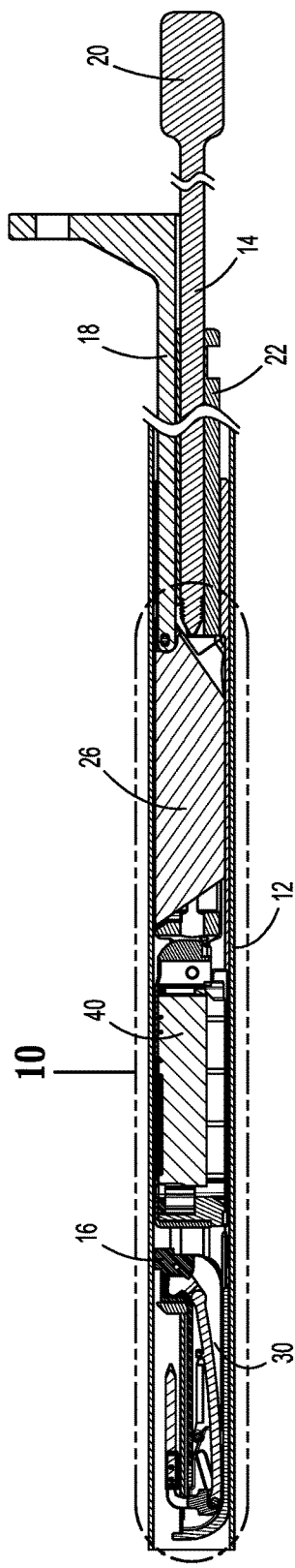
FIG. 9 is a cross-sectional view of the surgical stapling system of FIG. 1 as taken along section line 9-9 shown in FIG. 6.
Figure 10:
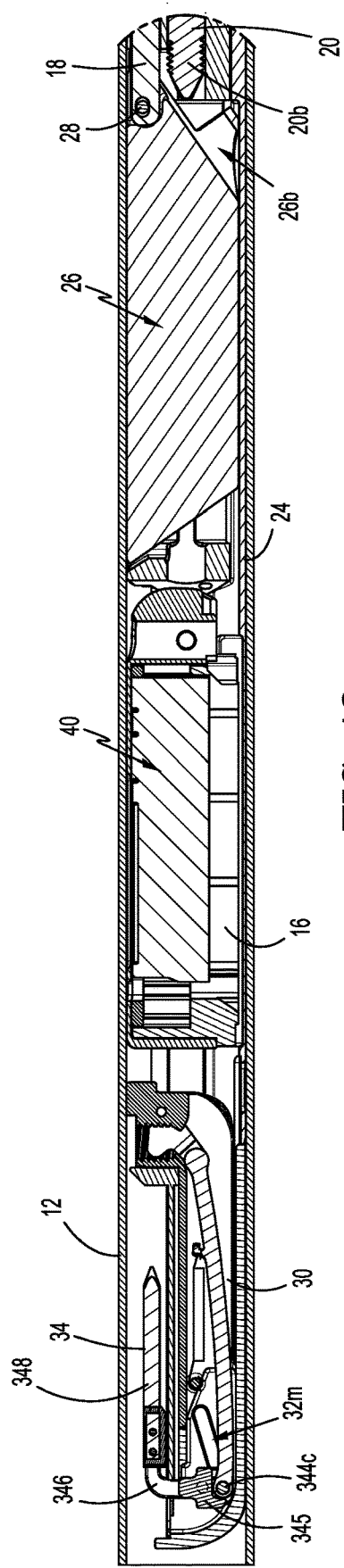
FIG. 10 is an enlarged view of the indicated area of detail shown in FIG. 9.
Figure 12:
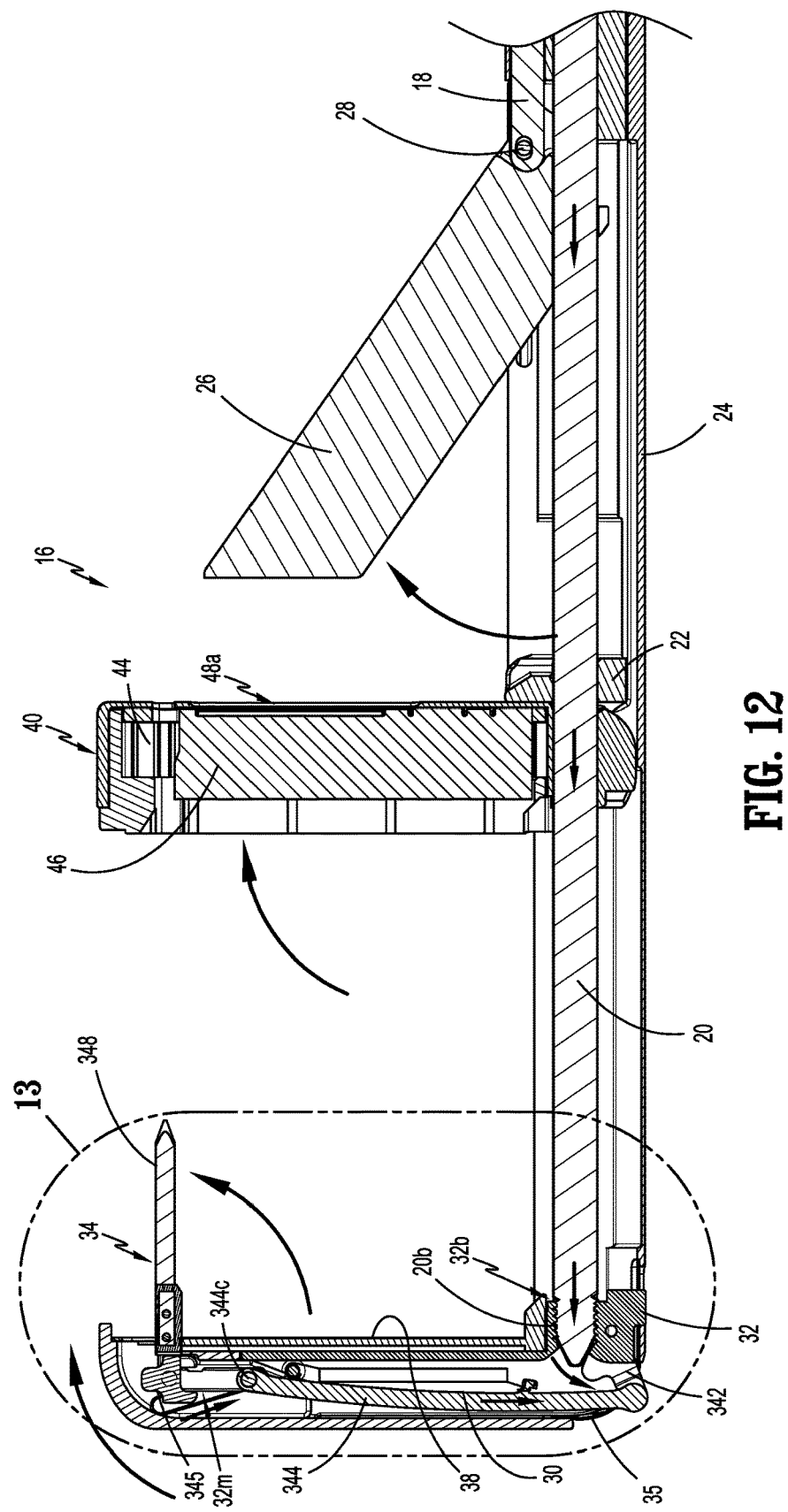
Figure 13:
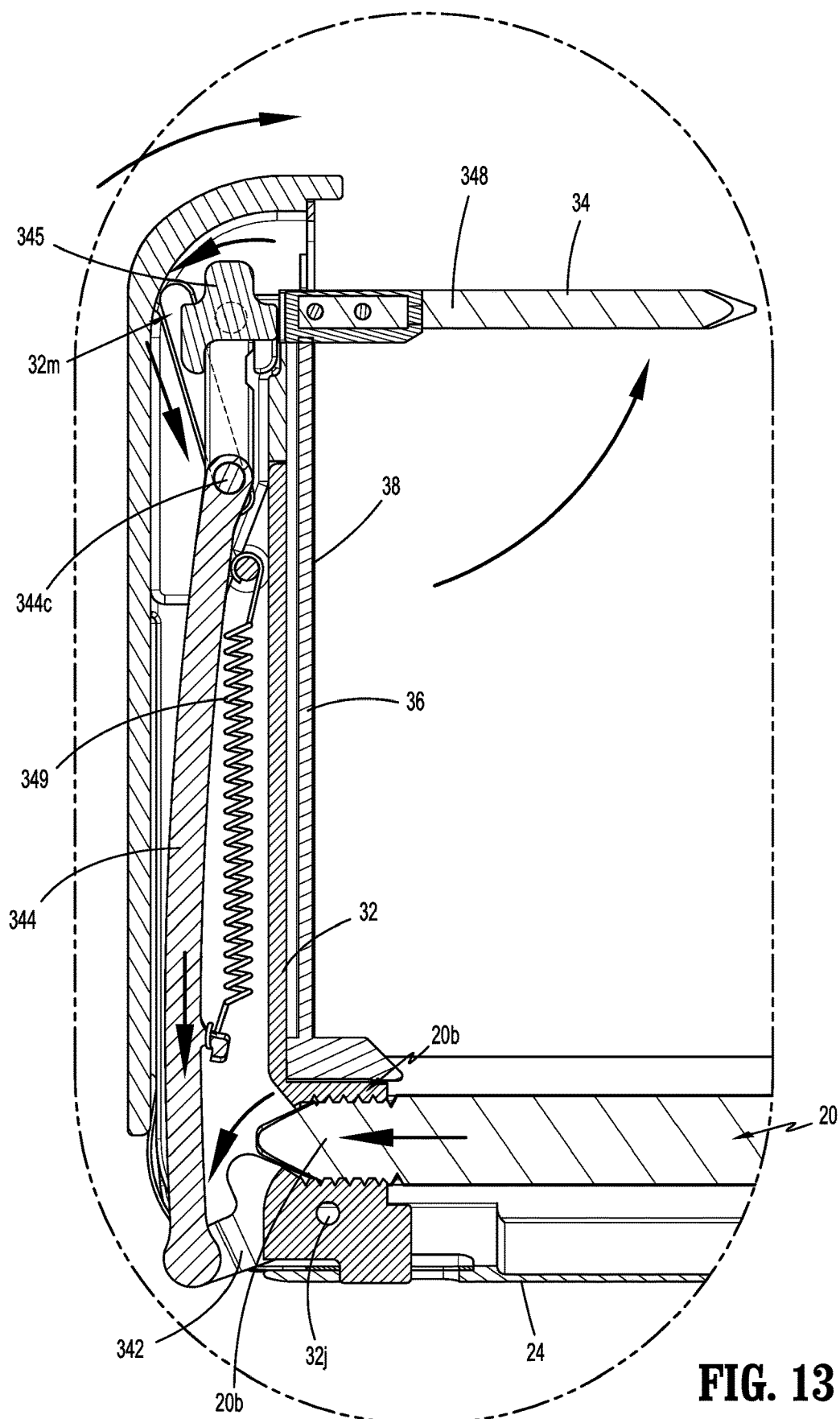
Figure 14:
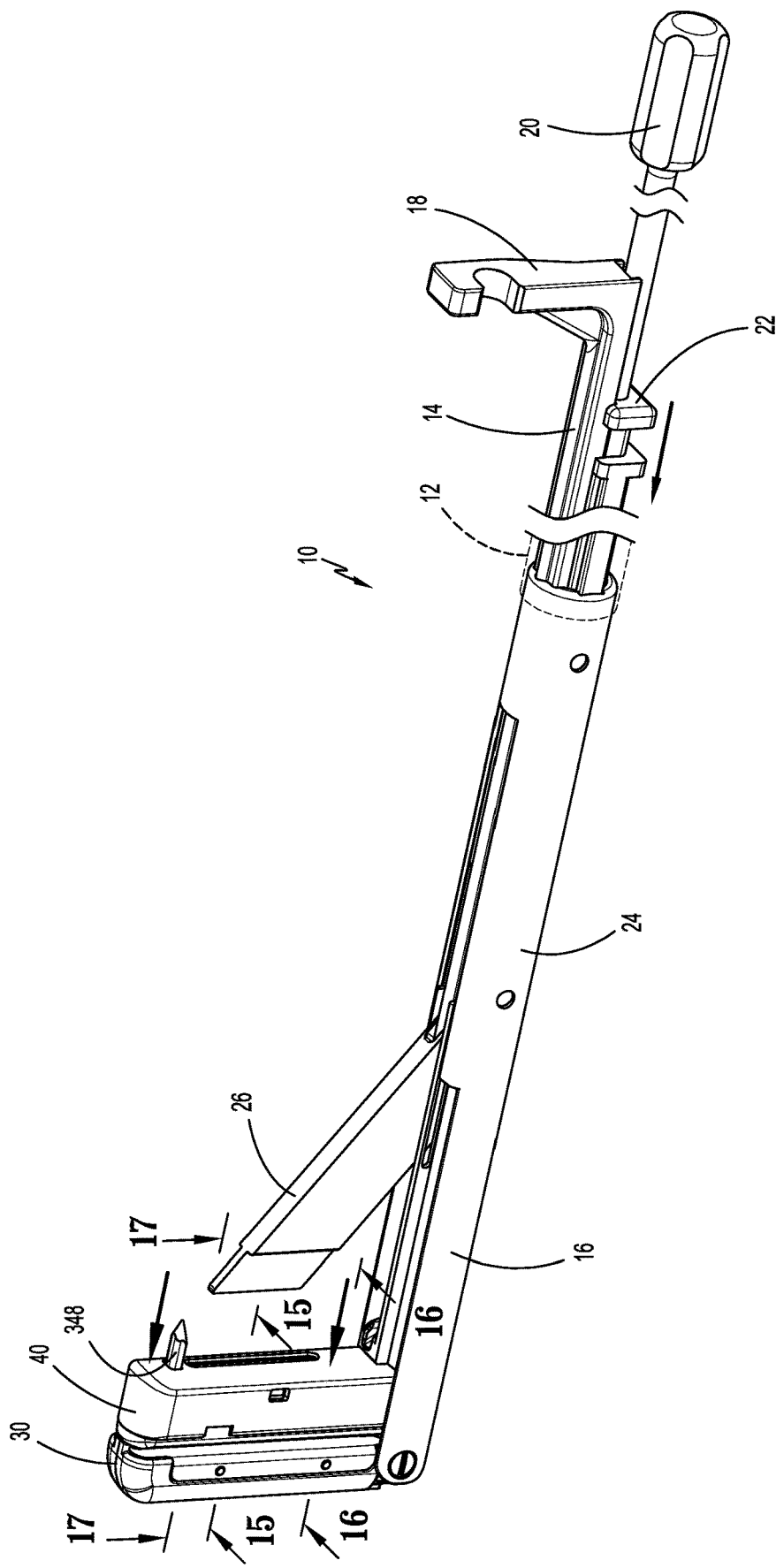
Figure 20:
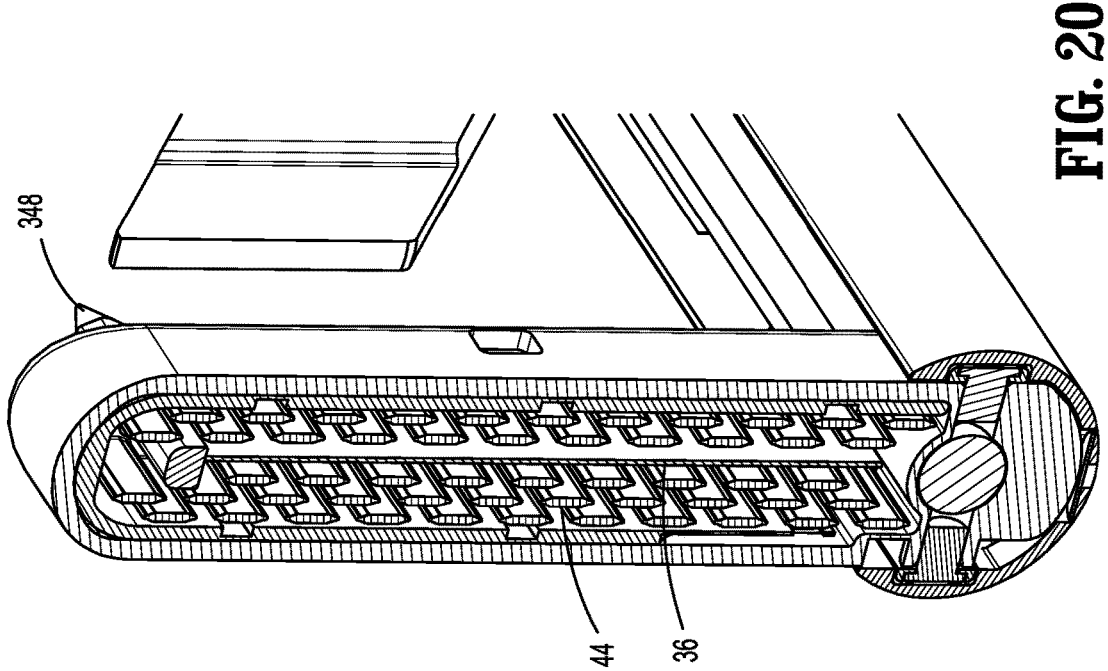
Figure 19:
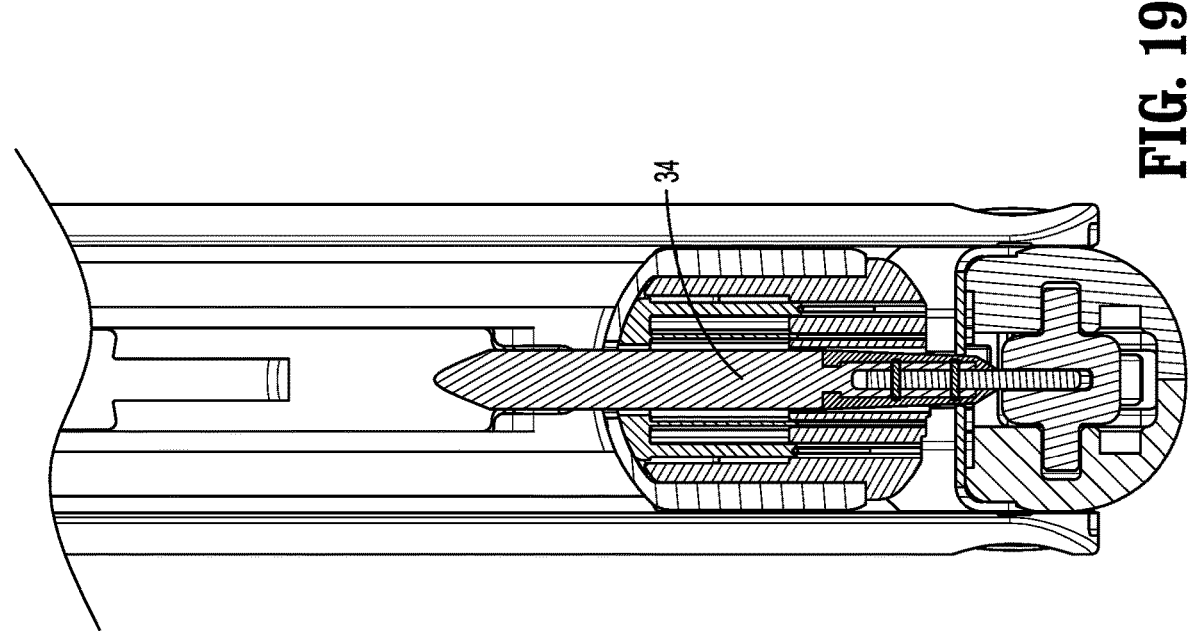
Figure 21:
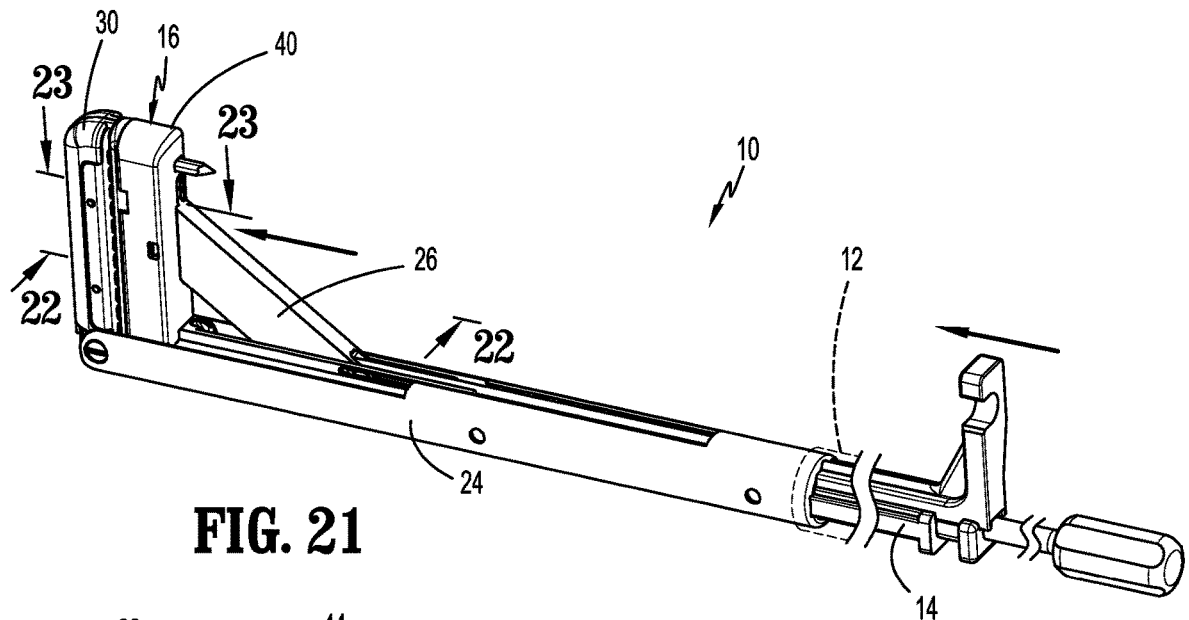
Figure 22:
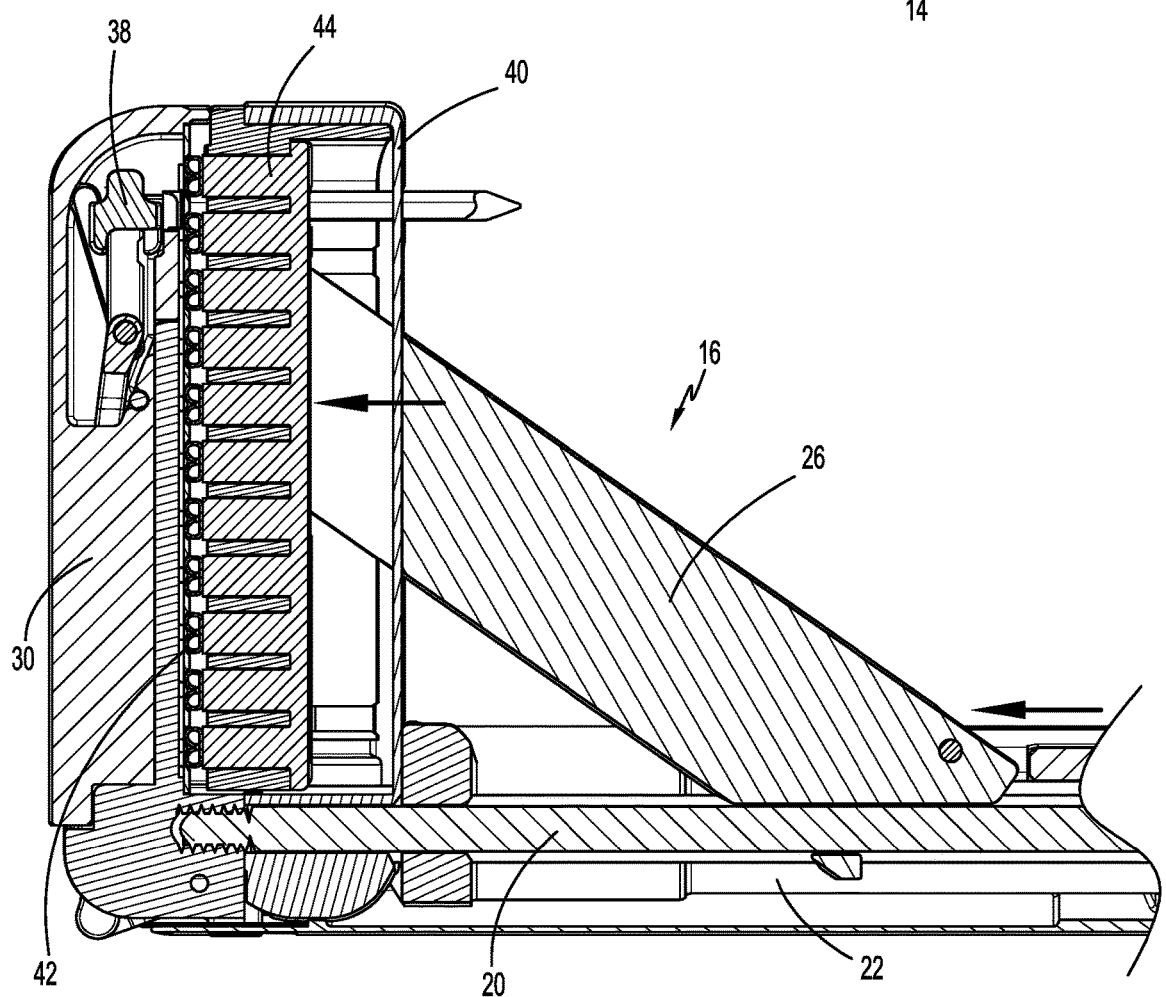

As shown in FIGS. 1-24, in use, surgical stapling apparatus 10 is inserted through a surgical cannula assembly 99 and into tissue "T" with anvil and cartridge assemblies 30, 40 in retracted positions (see FIG. 8). In the retracted position, the anvil and cartridge assemblies 30, 40 are oriented such that the respective lengths of anvil and cartridge assemblies 30, 40 are disposed in parallel relation with the longitudinal axis "L" of surgical stapling apparatus 10 for reducing a profile of surgical stapling apparatus 10 for easy insertion through a sealed passaged defined through surgical cannula assembly 99. With the surgical stapling apparatus 10 positioned in vivo adjacent a surgical site, housing tube 12 can be retracted proximally so that anvil and cartridge assemblies 30, 40 are urged toward their respective extended positions (see FIGS. 11 and 12) by leaf spring 35 and torsion springs 22g (see FIG. 2), respectively. Locking rod 20 can be translated axially through angled rod channel 26b of firing wedge 26 to cause firing wedge 26 to pivot about pivot pin 28 toward an extended position thereof relative to distal tube 24. With locking rod 20 positioned through firing wedge 26, locking rod 20 locks firing wedge 26 in the extended position thereof (e.g., at an acute angle relative to longitudinal axis "L"). Continued distal advancement of locking rod 20 through threaded rod passage 48b of cartridge assembly 40, by translation and rotation of locking rod 20 relative to longitudinal axis "L," locks cartridge assembly 40 in the extended position thereof. Locking rod 20 is then distally advanced into threaded engagement with threaded rod aperture 32b of anvil assembly 30, locking anvil assembly 30 in the extended position thereof.

Continued rotation of locking rod 20, namely, distally threading threaded tip 20b of locking rod 20 into threaded rod aperture 32b, causes threaded tip 20b of locking rod 20 to engage pivot plate 342 of alignment pin assembly 34 so that pivot plate 342 rotates downwardly about pivot pin 32j drawing drive arm 344 downwardly against the bias of compression spring 349 so that elbow 346 pivots alignment pin 348 to an extended position thereof as pivot pin 344c slides downwardly along angled slide channels 32m of first and second housings 32, 37. With alignment pin 348 in an extended position and disposed transverse to anvil 38 of anvil assembly 30, clamping rod 22 can be axially advanced to move cartridge assembly 40 toward anvil assembly 30 to capture tissue therebetween. Finally, firing rod 18 is advanced distally so that firing tooth 26c of firing wedge 26 is received within elongated wedge channel 48a of cartridge assembly 40 to drive pusher 44, staples 42, and knife 36 distally for securing staples 42 to the clamped tissue and for cutting the clamped and stapled tissue. Firing rod 18, locking rod 20, and clamping rod 22 can be drawn proximally relative to distal tube 24 and housing tube 12 can be advanced distally relative to distal tube 24 to enable anvil and cartridge assemblies 30, 40 (and firing wedge 26) to move from the extended positions thereof back to the retracted positions thereof. When the components of surgical stapling system 10 are disposed in the retracted positions thereof, surgical stapling system 10 can be withdrawn from surgical cannula assembly 10.

As those skilled in the art reading this disclosure will appreciate, the various aspects disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

As can be appreciated, securement of any of the components of the disclosed systems can be effectuated using known securement techniques such welding, crimping, gluing, fastening, etc.

Persons skilled in the art will understand that the structures and methods specifically described herein and illustrated in the accompanying figures are non-limiting exemplary aspects, and that the description, disclosure, and figures should be construed merely as exemplary of particular aspects. It is to be understood, therefore, that this disclosure is not limited to the precise aspects described, and that various other changes and modifications may be effectuated by one skilled in the art without departing from the scope or spirit of the disclosure. Additionally, it is envisioned that the elements and features illustrated or described in connection with one exemplary aspect may be combined with the elements and features of another without departing from the scope of this disclosure, and that such modifications and variations are also intended to be included within the scope of this disclosure. Indeed, any combination of any of the disclosed elements and features is within the scope of this disclosure. Accordingly, the subject matter of this disclosure is not to be limited by what has been particularly shown and described.

What is claimed is:

1. A transverse surgical stapling system, comprising:
an elongated shaft assembly;
a distal tube having a proximal end portion and a distal end portion, the proximal end portion of the distal tube supporting the elongated shaft assembly;
an anvil assembly being supported on the distal end portion of the distal tube and being spring biased toward the extended position by a leaf spring; and
a cartridge assembly supported on the distal tube in movable relation to the anvil assembly, wherein the anvil and cartridge assemblies are movable between retracted and extended positions relative to the distal tube.

2. The transverse surgical stapling system of claim 1, wherein the cartridge assembly is spring biased toward the extended position thereof by a torsion spring.

3. The transverse surgical stapling system of claim 1, wherein the elongated shaft assembly includes a locking rod that is receivable by the anvil and cartridge assemblies to lock the anvil and cartridge assemblies in the extended positions thereof.

4. The transverse surgical stapling system of claim 1, wherein the elongated shaft assembly includes a clamping rod that is pivotally coupled to the cartridge assembly, the clamping rod being positioned to translate the cartridge assembly relative to the anvil assembly.

5. The transverse surgical stapling system of claim 1, wherein the anvil assembly includes an alignment pin assembly that is positioned to engage the cartridge assembly.

6. The transverse surgical stapling system of claim 5, wherein the alignment pin assembly includes an alignment pin that is pivotally coupled to the anvil assembly and positioned to move between a retracted position within the anvil assembly and an extended position in which the alignment pin extends from the anvil assembly transverse to an anvil of the anvil assembly.

7. A transverse surgical stapling system, comprising:
- an elongated shaft assembly including a firing rod;
- a distal tube having a proximal end portion and a distal end portion, the proximal end portion of the distal tube supporting the elongated shaft assembly;
- an anvil assembly being supported on the distal end portion of the distal tube; and
- a cartridge assembly being supported on the distal tube in movable relation to the anvil assembly, the anvil and cartridge assemblies being movable relative to the distal tube between a retracted position and an extended position, wherein the firing rod translates through the distal tube to fire the staples from the cartridge assembly, the firing rod including a firing wedge coupled to the firing rod, wherein the firing wedge is positioned to pivot between a retracted position within the distal tube and an extended position in which a distal end of the firing wedge extends from the distal tube at an acute angle relative to the distal tube.

8. The transverse surgical stapling system of claim 7, wherein the firing wedge is pivotally coupled to a distal end portion of the firing rod, the firing wedge positioned to engage the cartridge assembly.

9. The transverse surgical stapling system of claim 7, wherein the cartridge assembly is spring biased toward the extended position by at least one of a torsion spring or a leaf spring.

10. The transverse surgical stapling system of claim 7, wherein the elongated shaft assembly includes a locking rod that is receivable by the anvil and cartridge assemblies to lock the anvil and cartridge assemblies.

11. The transverse surgical stapling system of claim 7, wherein the elongated shaft assembly includes a clamping rod that is coupled to the cartridge assembly, the clamping rod being positioned to move the cartridge assembly relative to the anvil assembly.

12. The transverse surgical stapling system of claim 7, wherein the anvil assembly includes an alignment pin that is positioned to engage the cartridge assembly.

13. The transverse surgical stapling system of claim 12, wherein the alignment pin is pivotally coupled to the anvil assembly.

14. A transverse surgical stapling system, comprising:
- a distal tube defining a longitudinal axis;
- an outer tube being slidably supported on the distal tube;
- an elongated shaft assembly;
- a cartridge assembly supporting a plurality of staples; and
- an anvil assembly being supported on the distal tube, the anvil assembly being pivotable between a retracted position aligned with the distal tube and an extended position in which the anvil assembly extends transverse to the distal tube, wherein in the extended position, the anvil assembly is positioned to form the staples supported in the cartridge assembly, the anvil assembly including an alignment pin that is pivotally coupled to the anvil assembly and positioned to move between a retracted position and an extended position for selectively engaging the cartridge assembly.

15. The transverse surgical stapling system of claim 14, wherein the elongated shaft assembly includes a firing rod that moves through the distal tube to fire the staples from the cartridge assembly.

16. The transverse surgical stapling system of claim 15, wherein the firing rod includes a firing wedge coupled to the firing rod, the firing wedge being positioned to engage the cartridge assembly.

17. The transverse surgical stapling system of claim 16, wherein the firing wedge is positioned to move between a retracted position within the distal tube and an extended position in which a distal end of the firing wedge extends from the distal tube.

18. The transverse surgical stapling system of claim 14, wherein the anvil assembly is spring biased toward the extended position by a leaf spring.

* * * * *